US00PP33012P2

(12) United States Plant Patent
Heuger

(10) Patent No.: US PP33,012 P2
(45) Date of Patent: Apr. 27, 2021

(54) ***HELLEBORUS* PLANT NAMED 'COSEH 7300'**

(50) Latin Name: ***Helleborus niger* X *Helleborus* x *hybridus***
Varietal Denomination: COSEH 7300

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/873,636

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. Anne Whealy

(57) ABSTRACT

A new and distinct cultivar of *Helleborus* plant named 'COSEH 7300', characterized by its upright to slightly outwardly spreading and mounded plant habit; moderately vigorous growth habit; dark green-colored leaves; moderately freely flowering habit; large dark greyed purple-colored flowers; and good garden performance.

2 Drawing Sheets

Figure 1:
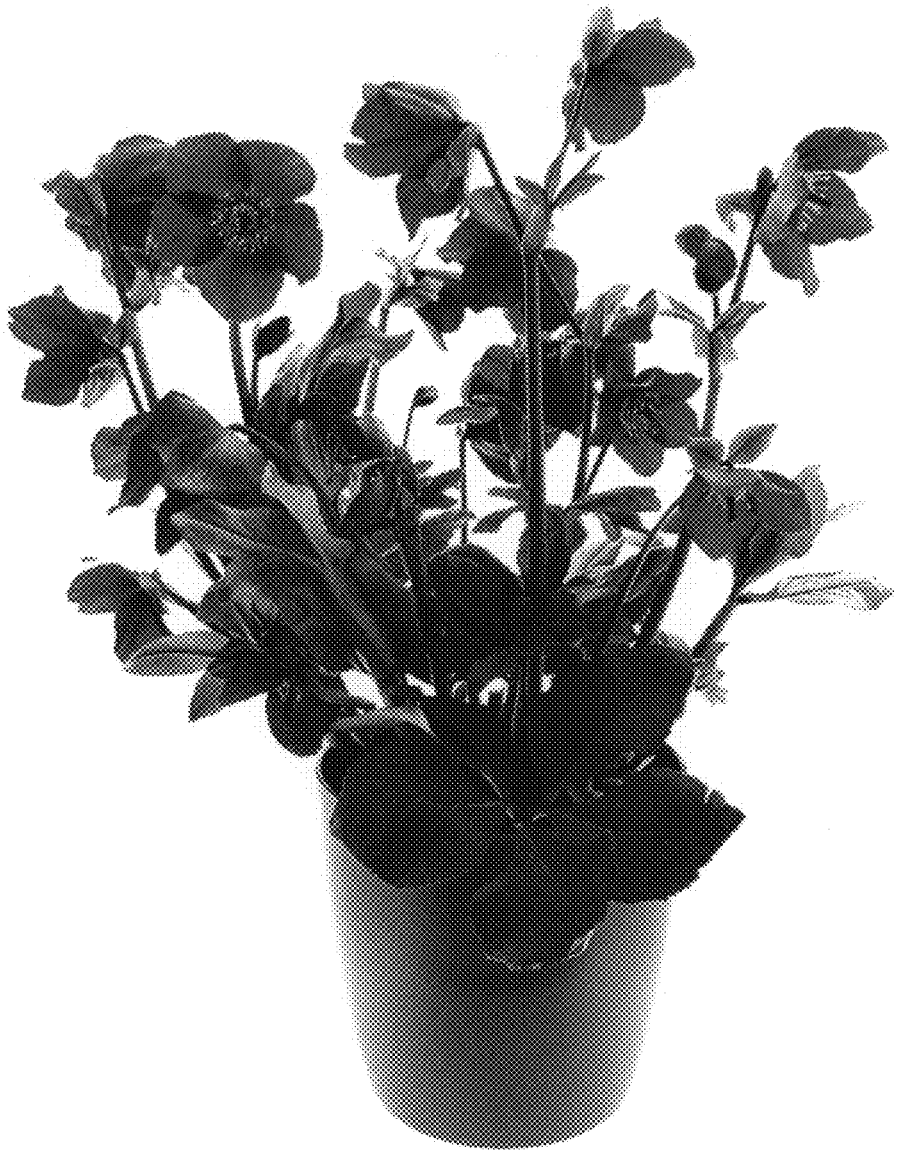

Botanical designation: *Helleborus niger* X *Helleborus* x *hybridus*.

Cultivar denomination: 'COSEH 7300'.

CROSS-REFERENCED TO CLOSELY-RELATED APPLICATIONS

Title: *Helleborus* Plant Named 'COSEH 7400'
Inventor/Applicant: Josef Heuger
Filed: Concurrently with the instant application Ser. No. 16/873,635
Title: *Helleborus* Plant Named 'COSEH 8100'
Inventor/Applicant: Josef Heuger
Filed: Concurrently with the instant application Ser. No. 16/873,649

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1390. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 7300'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in January, 2013 of a proprietary selection of *Helleborus niger* identified as code number P780, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in December, 2014.

Asexual reproduction of the new *Helleborus* plant by divisions in a controlled environment in Glandorf, Germany since March, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 7300'. These characteristics in combination distinguish 'COSEH 7300' as a new and distinct *Helleborus* plant:

1. Upright to slightly outwardly spreading and mounded plant habit.
2. Moderately vigorous growth habit.
3. Dark green-colored leaves.
4. Moderately freely flowering habit.

5. Large dark greyed purple-colored flowers.
6. Good garden performance.

Plants of the new *Helleborus* differ from plants of the female parent selection in the following characteristics:

1. Plants of the new *Helleborus* are more vigorous than plants of the female parent selection.
2. Flowers of plants of the new *Helleborus* are dark greyed purple in color whereas flowers of plants of the female parent selection are white in color.

Plants of the new *Helleborus* differ from plants of the male parent selection in the following characteristics:

1. Plants of the new *Helleborus* are more vigorous than plants of the male parent selection.
2. Flowers of plants of the new *Helleborus* are larger than flowers of plants of the male parent selection.

Plants of the new *Helleborus* can be compared to plants of *Helleborus niger* X *Helleborus* x *hybridus* 'COSEH 7400', disclosed in a U.S. Plant Patent application filed concurrently. Plants of the new *Helleborus* differ primarily from plants of 'COSEH 7400' in flower color as plants of new *Helleborus* are dark greyed purple in color whereas flowers of plants of 'COSEH 7400' are light yellow green to white in color.

Plants of the new *Helleborus* can be compared to plants of *Helleborus niger* X *Helleborus* x *hybridus* 'COSEH 8100', disclosed in a U.S. Plant Patent application filed concurrently. Plants of the new *Helleborus* differ primarily from plants of 'COSEH 8100' in flower color as flowers of plants of the new *Helleborus* are dark greyed purple in color whereas flowers of plants of 'COSEH 8100' are red purple and greyed purple in color. In addition, plants of the new *Helleborus* have larger flowers than plants of 'COSEH 8100'.

Plants of the new *Helleborus* can also be compared to plants of *Helleborus niger* X *Helleborus* x *hybridus* 'LEM 100', disclosed in U.S. Plant Pat. No. 25,646. In side-by-side comparisons, plants of the new *Helleborus* differ primarily from plants of 'LEM 100' in the following characteristics:

1. Plants of the new *Helleborus* are more vigorous than and not as compact as plants of 'LEM 100'.
2. Plants of the new *Helleborus* differ from plants of 'LEM 100' in flower color as plants of the new *Helleborus* have darker colored flowers than plants of 'LEM 100'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 7300' grown in a container.

Figure 2:
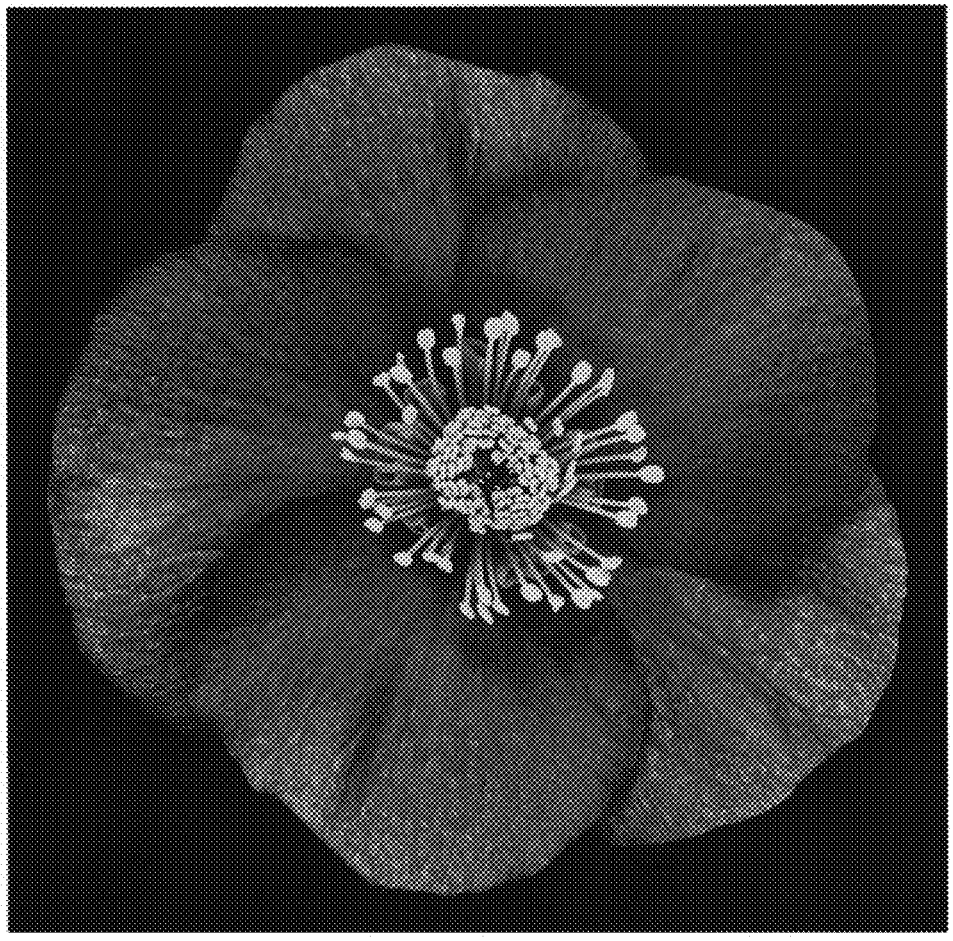

The photograph on the second sheet (FIG. 2 of 2) is a close-up view of a typical flower of 'COSEH 7300'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 7300'.

Parentage:

*Female, or seed, parent*.—Proprietary selection of *Helleborus niger* disclosed as code number P780, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to slightly outwardly spreading and mounding plant habit with flowers held within and above the foliar plane; plant shape, roughly flattened globular; moderately vigorous growth habit and moderate growth rate.

*Plant height, soil level to top of foliar plane*.—About 21 cm.

*Plant height, soil level to top of flowers*.—About 45 cm.

*Plant diameter* (*area of spread*): About 45.9 cm.

Leaf description:

*Arrangement*.—Leaves arranged in a basal rosette; leaves palmately compound with typically five leaflets per leaf.

*Leaf length*.—About 17.7 cm.

*Leaf width*.—About 22.8 cm.

*Leaflet length*.—About 11.2 cm.

*Leaflet width*.—About 5.3 cm.

*Leaf shape*.—Palmate; reniform in outline.

*Leaflet shape*.—Elliptic to obovate.

*Leaflet apex*.—Acute.

*Leaflet base*.—Attenuate.

*Leaflet margin*.—Serrate; coarsely undulate.

*Leaflet texture and luster, upper surface*.—Smooth, glabrous; leathery; glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to between 137A and NN137B; midvein tinged at the base with close to 183A to 183B. Developing leaflets, lower surface: Close to 146A; midvein, close to 178B. Fully developed leaflets, upper surface: Slightly darker than between NN137A and 147A; venation, close to 144A. Fully developed leaflets, lower surface: Close to 147B; venation, close to 145A.

*Petioles*.—Length: About 11.2 cm. Diameter: About 6 mm to 9 mm. Strength: Strong. Texture and luster, upper and lower surfaces: Smooth, glabrous; slightly glossy. Color, upper surface: Close to 144A slightly covered with fine dots, close to 177A to 177B. Color, lower surface: Close to 144A slightly covered with fine dots, close to 177A to 177B; proximally, more heavily covered with fine dots, close to between N186C and 200B.

Flower description:

*Flower shape and habit*.—Rotate flowers; flowers moderately cupped; arranged in panicles; moderately freely flowering habit with about two flowers per inflorescence and about 22 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 2.6 cm. Diameter: About 1.3 cm. Shape: Narrowly oblong. Texture and luster: Smooth, glabrous; matte. Color: Close to between 195B and 196A; towards the apex, close to 70A; venation, close to 61B.

*Inflorescence height* (*including peduncle*).—About 42.3 cm.

*Inflorescence diameter*.—About 16.7 cm.

*Flower diameter*.—About 9.4 cm by 9.4 cm.

*Flower depth* (*height*).—About 2.7 cm.

*Petals*.—All petals are transformed into nectaries.

*Sepals*.—Quantity and arrangement: About five, arranged in a single whorl. Length: About 5.1 cm. Width: About 3.6 cm. Shape: Broadly elliptic, slightly concave. Apex: Obtuse. Base: Truncate to broadly cuneate. Margin: Entire; slightly undulate. Texture and luster, upper surface: Smooth, glabrous; matte. Texture and luster, lower surface: Smooth, glabrous; slightly glossy. Color: When opening, upper surface: Close to 60D and 186A flushed with 186C to 186D; towards the margins and apex, close to 60C. When opening, lower surface: Close to 145D; towards the margins, strongly tinged with close to 60B to 60C. Fully opened, upper surface: Close to N77B, 186A and 186B flushed with close to 186D; venation, similar to lamina; with development, color becoming closer to N186C to N186D and towards the base, close to 144B. Fully opened, lower surface: Close to 186B; venation, close to 187C; with development, color becoming closer to N186C and venation, close to N186B.

*Flower bracts*.—Quantity per flower: Typically one or two. Length: About 5.3 cm. Width: About 3.9 cm. Shape: Ovate. Apex: Bluntly acute to tri-lobed. Base: Truncate. Margin: Entire; slightly undulate. Color, upper surface: Close to NN137A; venation, similar to lamina. Color, lower surface: Close to between 137C and 146A; venation, close to 183A.

*Peduncles*.—Length: About 25.9 cm. Diameter: About 9 mm. Aspect: About 10° from vertical. Strength: Strong. Texture and luster: Smooth, glabrous; glossy. Color: Close to 144B, heavily covered with fine dots, close to N186C.

*Pedicels*.—Length: About 2.1 cm. Diameter: About 3 mm. Aspect: About 10° to 25° from peduncle axis. Strength: Moderately strong. Texture and luster: Smooth, glabrous; moderately glossy. Color: Close to 187A.

*Reproductive organs*.—Stamens: Quantity per flower: About 60. Filament length: About 1.4 cm. Filament color: Close to NN155C. Anther shape: Double and broadly reniform; basifixed. Anther size: About 2 mm by 2.5 mm. Anther color: Close to 150C. Pollen amount: Moderate. Pollen color: Close to 4D to lighter than 4D. Pistils: Quantity per flower: About seven to ten. Pistil length: About 1.5 cm. Stigma diameter: About 0.3 mm. Stigma shape: Club-shaped. Stigma color: Close to 157A. Style length: About 1.4 cm. Style color: Close to 187A. Ovary color: Close to 145C; rib, close to 187B. Nectaries (transformed petals): Quantity per flower: About 13 to 15. Length: About 1.3 cm. Diameter: About 4 mm. Shape: Tubular, flattened. Texture and luster, inner and outer surfaces: Smooth, glabrous; slightly glossy. Color, immature, inner surface: Close to 144C. Color, immature, outer surface: Close to 144C; basal spot, close to N199C. Color, mature, inner surface: Close to 144B; towards the apex, close to 150C; venation, similar to lamina; with development, becoming closer to 144B and towards the apex, close to 151D. Color, mature, outer surface: Close to 144B; towards the apex, close to 150C; basal spot, close to N199C; venation, similar to lamina; with development, becoming closer to 144B, towards the apex, close to 151D and basal spot, close to N199C.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 7300' as illustrated and described.

* * * * *